(12) United States Patent
Erickson et al.

(10) Patent No.: US 9,057,825 B2
(45) Date of Patent: Jun. 16, 2015

(54) OPTICAL TRAPPING APPARATUS, METHODS AND APPLICATIONS USING PHOTONIC CRYSTAL RESONATORS

(75) Inventors: David Erickson, Ithaca, NY (US); Yih-Fan Chen, Taipei (TW)

(73) Assignee: Cornell University, Ithaca, NY (US)

( * ) Notice: Subject to any disclaimer, the term of this patent is extended or adjusted under 35 U.S.C. 154(b) by 74 days.

(21) Appl. No.: 13/520,033

(22) PCT Filed: Oct. 7, 2011

(86) PCT No.: PCT/US2011/055364
§ 371 (c)(1), (2), (4) Date: Sep. 7, 2012

(87) PCT Pub. No.: WO2012/048220
PCT Pub. Date: Apr. 12, 2012

(65) Prior Publication Data
US 2013/0182995 A1    Jul. 18, 2013

Related U.S. Application Data

(60) Provisional application No. 61/391,193, filed on Oct. 8, 2010.

(51) Int. Cl.
*G02B 6/00* (2006.01)
*G02B 6/12* (2006.01)
(Continued)

(52) U.S. Cl.
CPC . *G02B 6/12* (2013.01); *B82Y 20/00* (2013.01); *G02B 6/1225* (2013.01);
(Continued)

(58) Field of Classification Search
CPC ........... G02B 2006/12061; G02B 2006/12147; G02B 6/12; G02B 6/1225; G02F 1/025; B01L 3/502761; G01N 15/10
See application file for complete search history.

(56) References Cited

U.S. PATENT DOCUMENTS 7,081,192 B1   7/2006  Wang et al.
7,384,797 B1 *  6/2008  Blair ............................ 436/524
(Continued)

FOREIGN PATENT DOCUMENTS

EP        1942341 A1    7/2008
WO        2008151224    12/2008

OTHER PUBLICATIONS

Serey et al.; Comparison of silicon photonic crystal resonator designs for optical trapping of nanomaterials; IOP Publishing Ltd., Nanotechnology 21 (2010) 305202 (8pp).
(Continued)

*Primary Examiner* — Rhonda Peace
(74) *Attorney, Agent, or Firm* — William Greener; Alek Szecsy; Bond, Schoeneck & King, PLLC

(57) ABSTRACT

A plurality of photonic crystal resonator optical trapping apparatuses and a plurality optical trapping methods using the plurality of photonic crystal resonator optical trapping apparatuses include located and formed over a substrate a photonic waveguide that is coupled (i.e., either separately coupled or integrally coupled) with a photonic crystal resonator. In a particular embodiment, the photonic waveguide and the photonic crystal resonator comprise a monocrystalline silicon (or other) photonic material absent any chemical functionalization. In another particular embodiment, the photonic waveguide and the photonic crystal resonator comprise a silicon nitride material which when actuating the photonic crystal resonator optical trapping apparatus with a 1064 nanometer resonant photonic radiation wavelength (or other resonant photonic radiation wavelength in a range from about 700 to about 1200 nanometers) provides no appreciable heating of an aqueous sample fluid that is analyzed by the photonic crystal resonator optical trapping apparatus.

23 Claims, 6 Drawing Sheets

(51) Int. Cl.
  *B82Y 20/00* (2011.01)
  *G02B 6/122* (2006.01)
  *G02F 1/025* (2006.01)
  *B01L 3/00* (2006.01)
  *G01N 15/10* (2006.01)
  *G01N 15/00* (2006.01)

(52) U.S. Cl.
  CPC .............. *G02B 2006/12061* (2013.01); *G02B 2006/12147* (2013.01); *G02F 1/025* (2013.01); *B01L 3/502761* (2013.01); *B01L 2200/0668* (2013.01); *B01L 2300/0654* (2013.01); *B01L 2400/0454* (2013.01); *G01N 2015/0053* (2013.01); *G01N 15/10* (2013.01); *G01N 2015/0038* (2013.01)

(56) References Cited

U.S. PATENT DOCUMENTS

| | | | |
|---|---|---|---|
| 7,444,053 B2 | 10/2008 | Schmidt et al. | |
| 7,515,804 B2 | 4/2009 | Kittaka et al. | |
| 7,521,769 B2 | 4/2009 | Cunningham | |
| 7,742,662 B2 | 6/2010 | Cunningham | |
| 7,796,262 B1* | 9/2010 | Wang et al. | 356/436 |
| 7,825,380 B2 | 11/2010 | Puscasu et al. | |
| 7,840,101 B2 | 11/2010 | Wong et al. | |
| 7,864,313 B2 | 1/2011 | Baumberg et al. | |
| 7,869,032 B2 | 1/2011 | Zhang et al. | |
| 7,961,315 B2 | 6/2011 | Cunningham et al. | |
| 7,968,836 B2 | 6/2011 | Cunningham et al. | |
| 7,995,890 B2 | 8/2011 | Schmidt et al. | |
| 8,293,177 B2* | 10/2012 | Chakravarty et al. | 422/82.11 |
| 8,580,200 B2* | 11/2013 | Chakravarty et al. | 422/82.11 |
| 8,623,284 B2* | 1/2014 | Chakravarty et al. | 422/82.11 |
| 2005/0201660 A1 | 9/2005 | Grot et al. | |
| 2006/0170931 A1* | 8/2006 | Guo et al. | 356/480 |
| 2007/0036479 A1* | 2/2007 | Beausoleil | 385/12 |
| 2010/0028898 A1 | 2/2010 | Aoki et al. | |
| 2010/0124787 A1 | 5/2010 | Nitkowski et al. | |
| 2010/0270481 A1 | 10/2010 | Wong et al. | |
| 2011/0028346 A1 | 2/2011 | Chakravarty et al. | |
| 2011/0039730 A1* | 2/2011 | Erickson et al. | 506/12 |
| 2012/0099817 A1* | 4/2012 | Quan et al. | 385/33 |
| 2013/0005604 A1* | 1/2013 | Chakravarty et al. | 506/9 |
| 2013/0005605 A1* | 1/2013 | Chakravarty et al. | 506/9 |
| 2013/0182995 A1* | 7/2013 | Erickson et al. | 385/14 |

OTHER PUBLICATIONS

Quan et al.; Photonic crystal nanobeam cavity strongly coupled to the feeding waveguide; Applied Physics Letters 96, 203102 (2010), American Institute of Physics.

McCutcheon et al.; Design of a silicon nitride photonic crystal nanocavity with a quality factor of one million for coupling to a diamond nanocrystal; Nov. 10, 2008/ vol. 16, No. 23 Optics Express.

Poon et al.; Large-scale-integrated silicon photonics using microdisk and microring resonators; The Hong Kong University of Science and Technology, Clear Water Bay, Hong Kong, Feb. 2, 2010.

Hu et al.; Optical trapping of dielectric nanoparticles in resonant cavities; Physical Review A 82, 053819 (2010), The American Physical Society.

Commissioner; Patent Cooperation Treaty, Notification of Transmittal of the International Search Report and the Written Opinion of the International Searching Authority, or the Declaration, Apr. 10, 2012.

* cited by examiner

OPTICAL TRAPPING APPARATUS, METHODS AND APPLICATIONS USING PHOTONIC CRYSTAL RESONATORS

CROSS-REFERENCE TO RELATED APPLICATION

This application is related to, and derives priority from, provisional patent application Ser. No. 61/391,193, filed 8 Oct. 2010 and titled Nanomanipulation Apparatus, Methods and Applications, the content of which is incorporated herein fully by reference.

STATEMENT OF GOVERNMENT INTEREST

The work described herein was funded by: (1) the National Institutes of Health under project ID 1R21EB009202; and (2) the Department of Energy under grant no. W911NF-07-1-0454. The United States Government has certain rights in the subject matter claimed herein.

BACKGROUND

1. Field of the Invention

Embodiments relate generally to optical trapping manipulation of nanoparticles. More particularly, embodiments relate to efficient optical trapping manipulation of nanoparticles.

2. Description of the Related Art

Manipulation of nanoparticles and small molecules is an evolving field of investigation and technology that has implications in diverse fields including but not limited to drug design, molecular diagnostics, disease diagnosis and environmental sampling.

Since nanoparticle and small molecule manipulation is itself an evolving field of investigation and technology, where potential applications of nanoparticle and small molecule nanomanipulation also continue to evolve, desirable are additional nanoparticle and small molecule manipulation apparatus and methods that provide efficient operation of the nanoparticle and small molecule nanomanipulation apparatus and methods.

SUMMARY

Embodiments include photonic crystal resonator optical trapping apparatuses and methods for optical trapping of nanoparticles and small molecules while using the photonic crystal resonator optical trapping apparatuses. Photonic crystal resonator optical trapping apparatuses in accordance with the embodiments may comprise any of several photonic crystal materials that include any of several periodic nanostructures (i.e., typically but not exclusively dielectric or metallo-dielectric nanostructures) that provide photonic crystal resonators. In addition, photonic crystal resonator optical trapping apparatuses in accordance with the embodiments may include a separately coupled photonic waveguide (i.e., where a photonic waveguide and a photonic crystal resonator are separated by a separation distance), or alternatively an integrally coupled photonic waveguide (i.e., an integral photonic waveguide that includes no separation distance of a photonic waveguide with respect to a photonic crystal resonator).

In a first particular embodiment, a photonic crystal resonator optical trapping apparatus includes a silicon photonic waveguide and a silicon photonic crystal resonator, each absent any chemical functionalization. In a second particular embodiment, a photonic crystal resonator optical trapping apparatus includes a silicon nitride integral photonic waveguide and a silicon nitride integral photonic crystal resonator which provide for optical trapping within an aqueous solution absent appreciable heating of the aqueous solution, since the integrated silicon nitride photonic waveguide and silicon nitride photonic crystal resonator may be used to transmit optical radiation at a wavelength of about 1064 nanometers (or alternatively in a range from about 700 to about 1200 nanometers, more preferably from about 750 to about 850 nanometers, or alternatively more preferably from about 960 to about 1070 nanometers, where the foregoing more preferable ranges take into consideration both radiation absorption by water and also biological cell photodamage) rather than at a wavelength of about 1550 nanometers as is typically used with a silicon photonic waveguide and a silicon photonic crystal resonator which appreciably heat an aqueous solution.

A particular optical trapping apparatus in accordance with the embodiments includes a photonic waveguide located over a substrate. This particular optical trapping apparatus also includes a photonic crystal resonator also located over the substrate and coupled with the photonic waveguide. The photonic crystal resonator includes a plurality of periodic structures located within the photonic crystal resonator, absent chemical functionalization of the photonic crystal resonator.

Another particular optical trapping apparatus in accordance with the embodiments includes a photonic waveguide located over a substrate. This other particular optical trapping apparatus also includes a photonic crystal resonator also located over the substrate and coupled with the photonic waveguide. The photonic crystal resonator includes a plurality of periodic structures located within the photonic crystal resonator and comprises a photonic material having a resonant wavelength that is not absorbed by a sample fluid used in the optical trapping apparatus.

A particular optical trapping method in accordance with the embodiments includes providing an optical trapping apparatus including: (1) a fluid channel located over a substrate; (2) a photonic waveguide located over the substrate and also within the fluid channel; and (3) a photonic crystal resonator also located over the substrate and also within the fluid channel, and also coupled with the photonic waveguide, absent chemical functionalization of the photonic resonator. This particular method also includes introducing a particle containing fluid into the fluid channel. This particular method also includes actuating the optical trapping apparatus by introducing resonant photonic radiation into the photonic waveguide to trap a particle from the particle containing liquid at least one of the photonic waveguide and the photonic crystal resonator.

Another particular optical trapping method in accordance with the embodiments includes providing an optical trapping apparatus including: (1) a fluid channel located over a substrate: (2) a silicon nitride photonic waveguide located over the substrate and also within the fluid channel; and (3) a silicon nitride photonic crystal resonator also located over the substrate, also within the fluid channel and also coupled with the photonic waveguide. This particular method also includes introducing a particle containing fluid into the fluid channel. This particular method also includes actuating the optical trapping apparatus by introducing resonant photonic radiation into the photonic waveguide to trap a particle from the particle containing fluid at least one of the photonic waveguide and the photonic crystal resonator while not appreciably heating the particle containing fluid.

Within the present disclosure, and in particular within the claims that follow, use of the terminology "over" with respect to a location and a positioning of a first layer or structure with respect to a second layer or structure is intended to mean that one of the layers or structures is above the other of the layers or structure (i.e., with respect to a substrate as a parallel base plane), but not necessarily in contact with the other of the layers or structures. In contrast, use of the terminology "upon" with respect to the location and the positioning of the first layer or structure with respect to the second layer or structure is intended to mean not only the particular overlying relationship between the particular layers or structures, but also contact between the particular first layer or structure and the particular second layer or structure so designated.

BRIEF DESCRIPTION OF THE DRAWINGS

The objects, features and advantages of the embodiments are understood within the context of the Detailed Description of the Embodiments, as set forth below. The Detailed Description of the Embodiments is understood within the context of the accompanying drawings, that form a material part of this disclosure, wherein.

DETAILED DESCRIPTION OF THE EMBODIMENTS

Non-limiting exemplary embodiments provide a class of photonic crystal resonator optical trapping apparatus that is capable of generating enhanced optical field gradients in three dimensions while simultaneously enhancing a trap stiffness due to an amplification of an optical trapping field within a photonic crystal resonator, thus enabling advanced particle handling and optical trapping nanomanipulation functionalities. Particular photonic crystal resonator optical trapping apparatus in accordance with the embodiments may be fabricated from monocrystalline silicon materials, or alternatively from silicon nitride materials (which are generally not monocrystalline, or polycrystalline, but rather generally amorphous). Other materials are not precluded for fabricating photonic crystal resonator optical trapping apparatuses in accordance with the illustrative non-limiting embodiments.

Particular photonic crystal resonator optical trapping apparatuses in accordance with the embodiments do not use chemical functionalization of either a coupled photonic waveguide (i.e., either a separately coupled photonic waveguide or an integrally coupled photonic waveguide) or a photonic crystal resonator, but rather rely upon physical near field optical trapping characteristics of at least one of the coupled photonic waveguide and the photonic crystal resonator absent chemical functionalization. Additional particular photonic crystal resonator optical trapping apparatuses in accordance with the embodiments provide for selection of materials of construction of a photonic waveguide and a photonic crystal resonator to provide for optical resonance at a wavelength not appreciably absorbed by a fluid that may be analyzed by the photonic crystal resonator optical trapping apparatus so that the fluid that may be analyzed by the photonic crystal resonator optical trapping apparatus is not appreciably heated (i.e., a temperature rise of less than about 1 degree centigrade) when analyzed by the photonic crystal resonator optical trapping apparatus.

Figure 1:
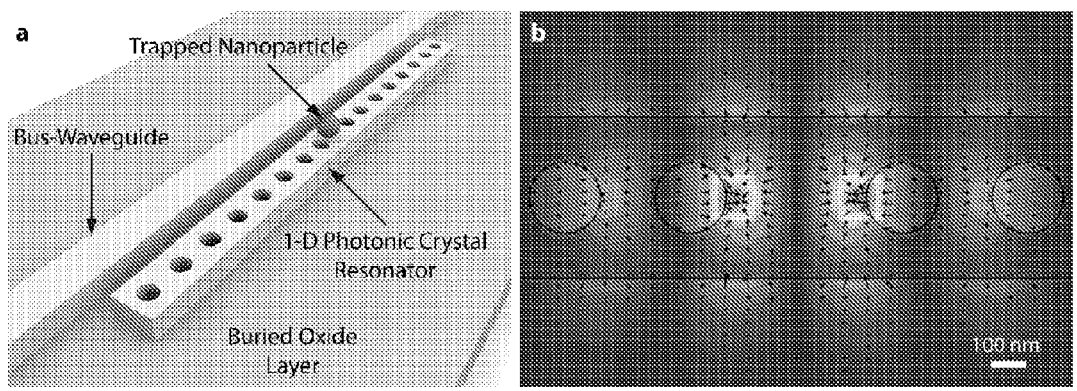
FIG. 1 shows: (1) a schematic perspective view diagram of a resonant optical trapping apparatus that includes located and separately coupled over a substrate a silicon photonic waveguide and a silicon photonic crystal resonator in accordance with a first embodiment; and (2) a three dimensional simulation of optical field operation of the resonant optical trapping apparatus that includes the separately coupled silicon photonic waveguide and the silicon photonic crystal resonator in accordance with the first embodiment.

I. Separately Coupled Photonic Waveguide Based Photonic Crystal Resonator Optical Trapping Apparatus Fabricated from Monocrystalline Silicon Materials As illustrated in FIG. 1a, a particular photonic crystal resonator optical trapping apparatus in accordance with a first embodiment includes, located and formed over a substrate (of which an upper surface comprises a buried oxide layer within a silicon-on-insulator substrate), a one-dimensional silicon photonic crystal resonator that is evanescently coupled to a single mode silicon bus photonic waveguide. A standing wave nature of a resonant optical field within the silicon photonic crystal resonator of the resonant optical trapping apparatus enables a true static point trap with strong field confinement in all three dimensions.

Figure 2:
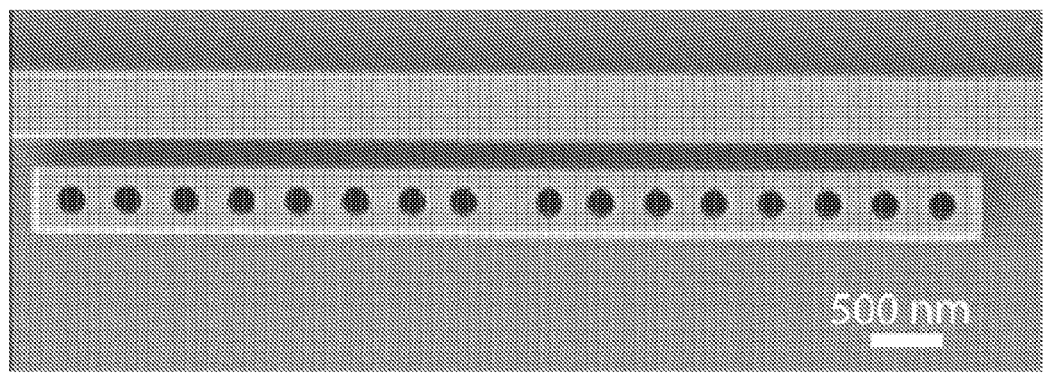
FIG. 2 shows a scanning electron microscopy (SEM) image of a photonic crystal resonator optical trapping apparatus in accordance with the first embodiment.

A scanning electron microscopy (SEM) image of a typical photonic crystal resonator optical trapping apparatus in accordance the first embodiment is shown in FIG. 2. A fabrication process for such a photonic crystal resonator optical trapping apparatus is provided in further detail below. Generally each of the single mode silicon bus photonic waveguide and the one dimensional silicon photonic crystal resonator is patterned from a surface silicon layer within a silicon-on-insulator substrate and has a thickness from about 200 to about 500 nanometers, a linewidth from about 200 to about 1000 nanometers and a separation distance from about 50 to about 400 nanometers. Moreover, the one-dimensional silicon photonic crystal resonator has a length from about 2 to about 10 microns and includes from about 6 to about 30 apertures (i.e., periodic structures that provide the photonic crystal resonator, and that typically comprise holes) located and formed penetrating through a top surface of the one-dimensional silicon photonic crystal resonator. The apertures will typically have a diameter from about 50 to about 400 nanometers, either uniformly sized or variably sized. A smaller sized aperture or hole from about 10 to about 100 nanometers may be beneficially located centered with respect to remaining apertures.

When light (i.e., photonic radiation) at a resonant wavelength is coupled into the silicon bus photonic waveguide, a stationary interference pattern is formed within the silicon photonic crystal resonator resulting in a tight confinement of an optical field in an extremely small volume, as illustrated in FIG. 1b (where the arrows indicate the direction and magnitude of local optical forces). These strong field gradients coupled with the resonant amplification of the optical field within the silicon photonic crystal resonator enables a stable trapping of nanoparticles ranging in size from 50 to 500 nm.

Figure 3:
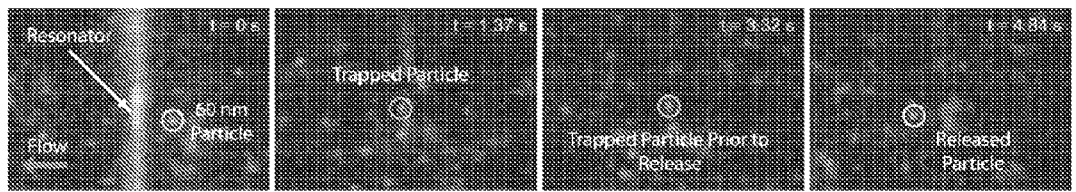
FIG. 3 shows the results of progressive process steps in trapping and release of a nanoparticle on a photonic crystal resonator optical trapping apparatus in accordance with the first embodiment.

FIG. 3 shows a series of fluorescence microscopy images that illustrate the trapping and release of a 62 nm polystyrene nanoparticle (refractive index n=1.59) with respect to a monocrystalline silicon based photonic crystal resonator optical trapping apparatus in accordance with the first embodiment. It is noted that foregoing 62 nm polystyrene nanoparticle is generally well below the size limit of a particle that might plausibly be trapped using alternative immobilization approaches. With respect to the images of FIG. 3, a tunable infrared laser was used to couple TE polarized light at a resonant wavelength of 1548.15 nm into an input end of a silicon crystal bus photonic waveguide using a lensed fiber. The output power at the silicon crystal bus photonic waveguide exit was measured to be 1.7 mW. Within the context of the foregoing experiment, a microfluidic flow convects particles along a channel and toward the silicon photonic crystal resonator. If a candidate particle passes within close proximity of the silicon photonic crystal resonator surface and the resonant optical field lobes, the candidate particle experiences a tweezing force due to the strong local field gradient resulting in the particle getting trapped at the silicon photonic crystal resonator surface. The trapped particle is subsequently released by turning the laser power off (as is shown FIG. 3 for the 62 nm case above). Trapped particles can also be released either by detuning the input wavelength away from a resonant wavelength, or by switching the polarization of light from TE to TM.

An interesting aspect of the photonic crystal resonator optical trapping apparatus design in accordance with at least this first embodiment is that a guided optical mode within a silicon (or possibly other photonic material) bus photonic waveguide possesses a forward momentum which enables the simultaneous trapping and propulsion of nanoparticles along its surface. In contrast, at resonance, the field within the silicon photonic crystal resonator consists of a tightly confined standing wave with no propagation component. Thus, by tailoring a microfluidic flow and exploiting this contrasting nature of the optical field within the silicon bus photonic waveguide and the one-dimensional silicon photonic crystal resonator, a novel technique for performing particle manipulations may be demonstrated.

Figure 4:
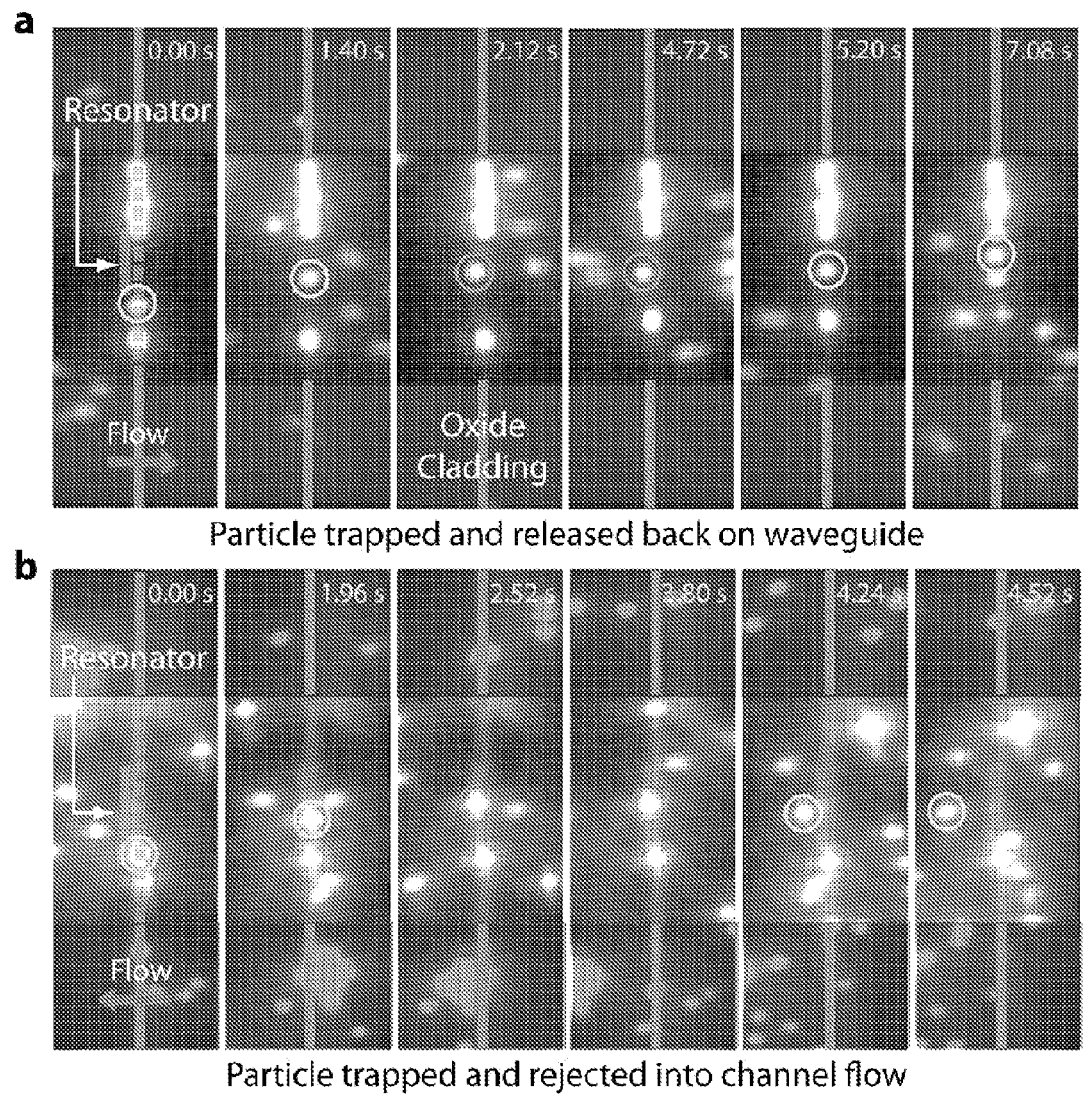
FIG. 4 shows a series of plan view diagrams of: (1) a particle trapping onto a photonic crystal resonator and release onto a photonic waveguide; and (2) a particle trapping onto a photonic crystal resonator and release into a fluid flow, in accordance with the first embodiment.

FIG. 4 illustrates a series of time-lapse fluorescence microscopy images demonstrating the trapping and manipulation of 500 nm polystyrene microspheres while using a photonic crystal resonator optical trapping apparatus in accordance with the first embodiment. In the top panel of FIG. 4 (i.e., FIG. 4a), a flow in a microfluidic channel is from left to right. A 500 nm polystyrene microsphere is trapped and transported along the silicon bus photonic waveguide by an evanescent field of the guided optical mode. The input light is initially tuned to the resonant wavelength. As a result, when a particle moves up along the silicon bus photonic waveguide and approaches the silicon photonic crystal resonator, the particle experiences a lateral tweezing force toward the silicon photonic crystal resonator center. Due to the field amplification within the silicon photonic crystal resonator and the stronger field gradients in the silicon photonic crystal resonator, the lateral tweezing force experienced by the particle is much stronger than the trapping force exerted by the silicon bus photonic waveguide. This results in the particle hopping from the silicon bus photonic waveguide to the silicon photonic crystal resonator center. Once trapped, the particle is held stationary on the silicon photonic crystal resonator. To release the particle back onto the silicon bus photonic waveguide, the silicon bus photonic waveguide input wavelength may be tuned away from resonance. This releases the particle from the silicon photonic crystal resonator trap, and the particle is convected with the fluid flow toward the silicon bus photonic waveguide. Since the silicon bus photonic waveguide is not wavelength selective, the evanescent field of the off-resonant guided optical mode retraps the particle as it passes above the surface of the silicon bus photonic waveguide. Once the particle is trapped on the silicon bus photonic waveguide, it is subsequently transported further along the silicon bus photonic waveguide. When a direction of fluid flow in the microchannel is reversed (FIG. 4B), the trapped particle on the silicon photonic crystal resonator can be rejected into the fluid flow when the input laser is tuned off resonance.

To characterize the trapping stiffness as well as the maximum trapping force in all three dimensions within a photonic crystal resonator optical trapping apparatus in accordance with the first embodiment, a detailed three-dimensional finite element numerical analysis has been undertaken using a commercial software package (COMSOL). The material properties of the silicon photonic crystal resonator and the surrounding water medium within a fluid channel were taken into consideration while solving for the electromagnetic field distribution at resonance. To determine the force exerted on a particle, a virtual spherical surface was constructed that enclosed the particle, and an electromagnetic field on this surface was calculated. By evaluating the time-independent Maxwell stress tensor and integrating it over the closed surface enclosing the particle, one is able to obtain the trapping force in various directions.

Figure 5:
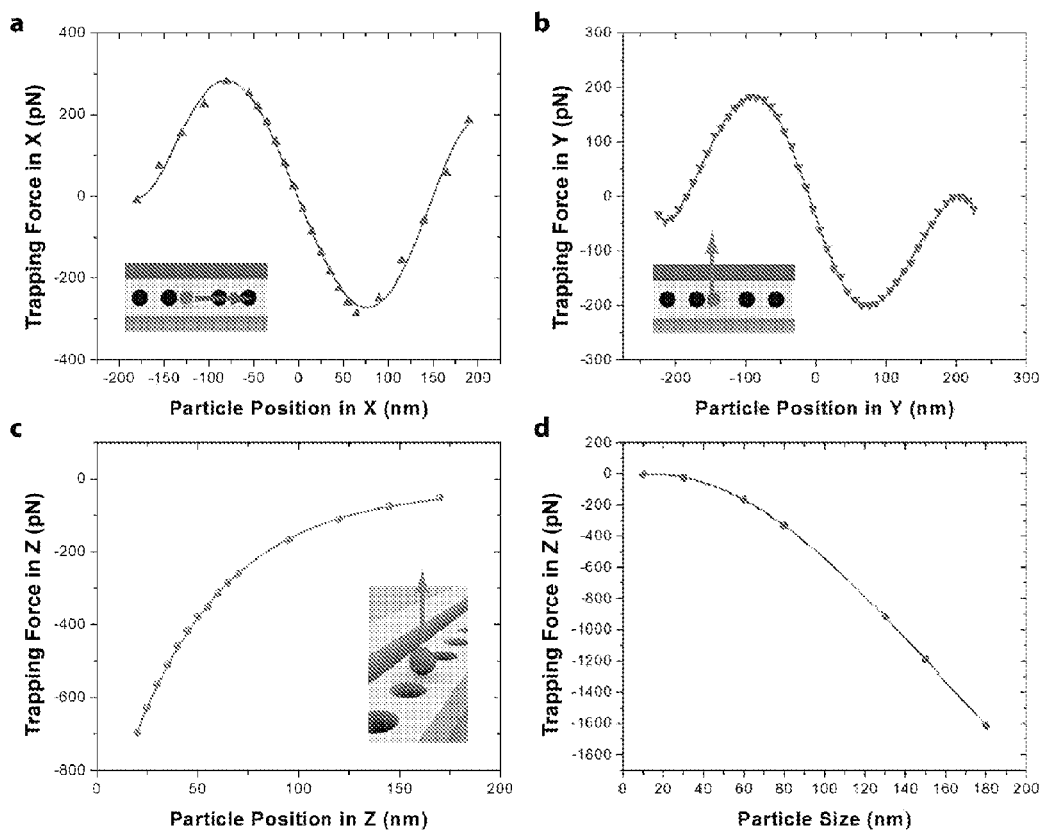
FIG. 5 shows a series of graphs of Trapping Force in X, Y and Z directions versus Particle Position in X, Y and Z directions (i.e., FIG. 5a, FIG. 5b and FIG. 5c) and Trapping force in a Z direction as a function of Particle Size (i.e., FIG. 5d) related to a numerical analysis of trapping forces within a photonic crystal resonator optical trapping apparatus in accordance with the first embodiment.

FIG. 5a, FIG. 5b and FIG. 5c illustrate the trapping force profile for a 100 nm polystyrene microsphere that is displaced in all three dimensions from a stable trapping position for 1 W of input optical trapping power. One may observe that the maximum trapping force for the 100 nm particle is 700 pN in the Z direction (evaluated 25 nm from the silicon photonic crystal resonator surface as illustrated in FIG. 5c). The required placement of a Maxwell stress tensor surface around the particle, as well as numerical meshing limitations, prevented the calculation of forces when the particle was closer than 25 nm with respect to the silicon photonic crystal resonator surface. A common figure of merit related to the quality of optical traps is a trap stiffness for a given particle size. From the graphs of FIG. 5 one may estimate a trap stiffness of 4.81, 3.30, and 8.53 pN nm$^{-1}$ W$^{-1}$ for the 100 nm polystyrene microsphere along the X, Y and Z axes, respectively, corresponding to a radial trap stiffness (in the X-Y plane) of 1.96 pN nm$^{-1}$ W$^{-1}$.

Figure 6:
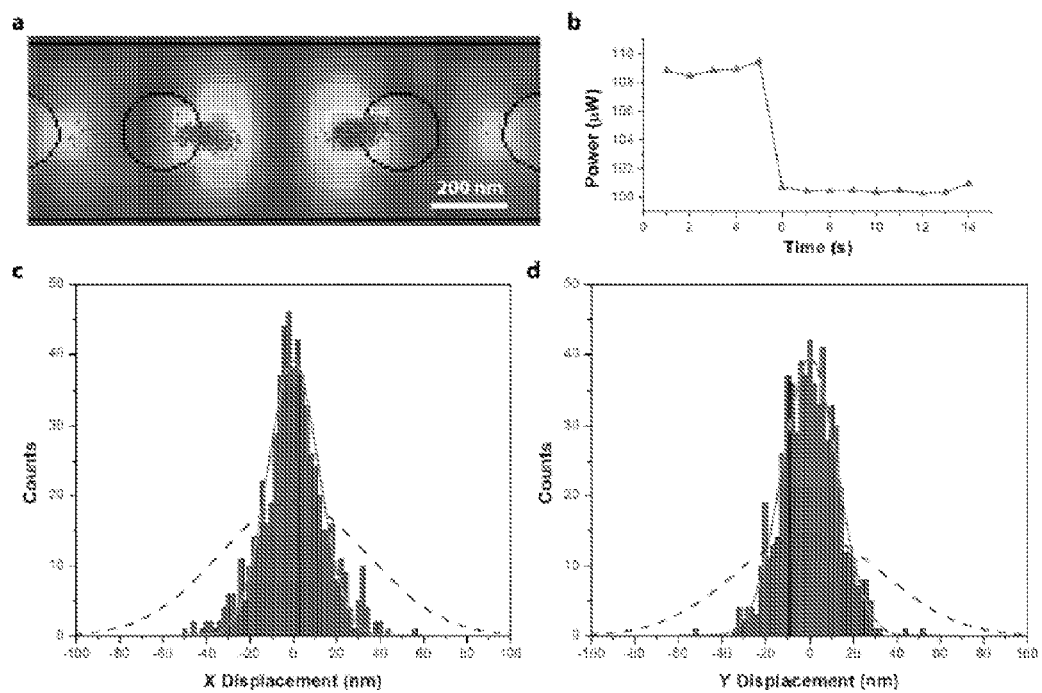
FIG. 6 shows a series of images (i.e., Brownian motion images in FIG. 6a, Power versus Time graph in FIG. 6b (i.e., illustrating particle release) and histograms in FIG. 6c and FIG. 6d (for estimating trapping stiffness) related to suppression of Brownian motion and trapping stiffness determination for nanoparticles trapped in accordance with the first embodiment.

To obtain experimental values for the trapping stiffness in the X and Y axes and compare them with theoretical estimates, the suppressed Brownian motion of a trapped 200 nm particle was studied. Triton X-100 (1%) was used as a surfactant to minimize stiction between the nanoparticle and the silicon photonic crystal resonator surface. FIG. 6a illustrates a scatter plot of the position trace of a 200 nm particle when the output power measured at the waveguide output was 140 µW. The scatter plot is overlaid on top of the field distribution within the silicon photonic crystal resonator (to scale). It is evident that at such low optical powers, the trapping is weak and the particle hops between the two center lobes of the resonant optical field. One can also observe that the particle hops to the weaker traps at the side lobes for a short duration of time. When the power is raised such that the measured power at the waveguide output is 175 µW, the strength of the trapping increases and the particle is observed to remain stably trapped at a single site. FIG. 6c and FIG. 6d show histograms for the displacement of a trapped 200 nm particle, each of which exhibits a Gaussian distribution. From these plots, one may determine a radial trapping stiffness of 2.86 pN nm$^{-1}$ W$^{-1}$, which is slightly lower than a numerical estimate of 5.38 pN nm$^{-1}$ W$^{-1}$ for a 200 nm particle (see additional information below). Since the experimentally observed trap stiffness agrees reasonably well with numerical estimates, one may infer that surface interactions between a particle and a photonic crystal resonator surface do not dominate the trapping characteristics. In general, one may observe a higher trap stiffness for larger particles, as they are influenced by a larger portion of an optical trapping field.

The estimated trapping stiffness for a resonant optical trapping apparatus in accordance with the first embodiment is an order of magnitude higher than that of slot waveguides (0.2 pN nm$^{-1}$ W$^{-1}$ for a 100 nm particle; see Yang et al., Nature 2009, 457, 71-759) and several orders of magnitude higher than other recent optical trapping techniques such as plasmonic tweezers (0.013 pN nm$^{-1}$ W$^{-1}$ for a 200 nm bead; see Grigorenko et al., Nat. Photonics, 2008, 2, 365-370.), conventional high-NA optical tweezers (0.16 pN nm$^{-1}$ W$^{-1}$ for a 500 nm bead; see Neuman et al., Rev. Sci. Instrum., 2004, 75, 2787-2809), and Fresnel zone plate optical tweezers (0.1 pN nm$^{-1}$ W$^{-1}$ for a 2 µm bead; see Schonbrun et al., Appl. Phys. Lett., 2008, 92, 071112-3). While it is difficult to make a clear comparison between these different trapping techniques due to the dependence of the trapping stiffness on particle size, it is evident that the stiffness of trapping within a photonic crystal resonator optical trapping apparatus in accordance with at least this first embodiment exceeds the state-of-the-art by at least an order of magnitude.

The presence of a trapped particle affects the resonant wavelength of the silicon photonic crystal resonator by a small amount. Thus, when a trapped particle escapes from the trap, it induces a slight shift in the resonant wavelength which manifests itself as a discrete jump in the output power from the coupled photonic waveguide. By monitoring the laser power at the output end of the coupled photonic waveguide, it is possible to infer the release of a particle from the optical trap, as shown in FIG. 6b. It is important to note that this effect is more pronounced in the case of larger nanoparticles. As the size of the nanoparticle reduces, an induced shift in the resonant wavelength also decreases.

A. Experimental Details

The photonic crystal resonator optical trapping devices and apparatus in accordance with the foregoing first embodiment were fabricated from silicon-on-insulator wafers having a device layer thickness of 250 nm. XR-1541 electron beam resist (HSQ, Dow-Corning Corporation) was spun on the wafer and the devices were patterned using a Leica VB6-HR electron beam lithography system. Details regarding the fabrication procedure of these devices are generally conventional, but in particular include the use of e-beam evaporated silicon oxide as a nanotaper cladding. A tunable infrared laser was connected to a tapered fiber lens via an erbium-doped-fiber-amplifier (EDFA) to produce enough optical power for performing these optical trapping experiments. Fluorescent polystyrene nanoparticles with diameters ranging from 50-500 nm (Duke Scientific) and refractive index 1.59 were mixed in a 100 mM phosphate buffer solution. 1% Triton X-100 surfactant was added to minimize adhesion and stiction issues between the polystyrene nanoparticles and the microfluidic channel surfaces, as well as the substrate of the chip. PDMS microfluidic channels were bonded to the chips after plasma treatment for 15 seconds. The channels were 120 µm wide and 5 µm tall. A syringe pump was used to control the fluid flow within the microfluidic channels. Measurements of the particle position and Brownian motion were made using the Video Spot Tracker software package.

B. Suppressed Brownian Motion and Trap Stiffness Measurement

In accordance with disclosure above, the radial trapping stiffness of a photonic crystal resonator optical trapping apparatus in accordance with the first embodiment was estimated by analyzing the suppressed Brownian motion of a trapped 200-nm polystyrene nanoparticle when the power at the output of a silicon bus photonic waveguide was measured to be 175 µW. For a particle in a harmonic potential with stiffness $k_x$, the equipartition theorem states that:

$$\tfrac{1}{2}k_b T = \tfrac{1}{2}k_x [x^2] \qquad (1)$$

where $k_b$ is the Boltzmann constant, T is the absolute temperature and $[x^2]$ is the positional variance of the trapped particle. By measuring the instantaneous position of the particle, it is possible to determine the stiffness of the optical trap. However, detection systems such as video cameras do not measure the instantaneous particle position. Instead, they introduce a bias in the measurements due to the finite integration time W of the device. Wong et al., Opt. Express, 2006 14, 12517-12531, performed a detailed experimental and theoretical analysis to demonstrate a novel method that accounts for these systematic biases introduced in measurements due to video-image motion blur. The true and measured variance var(X) and var($X_{meas}$) are related by:

$$var(X_{meas}) = var(X) S(\alpha) \qquad (2)$$

where $S(\alpha)$ is the motion blur correction function. $\alpha$ is given by $Wk_x/2\pi\gamma$ where $\gamma$ is the Stoke's drag coefficient and W is 51.17 ms. By combining equation (1) and equation (2) one may obtain:

$$var(X_{max}) = [(k_b T) W/2\pi\gamma]/[S(\alpha)/(\alpha)] \qquad (3)$$

Equation (3) may be solved numerically for a using values for var($X_{meas}$) and var($Y_{meas}$) determined from FIG. 6c and FIG. 6d. Thus one may obtain trap stiffness values along the X and Y axes of 3.73×10$^{-3}$ pN/nm and 3.50×10$^{-3}$ pN/nm respectively. One may also determine the true standard deviation of the Brownian fluctuations in the X and Y axes to be 33.2 nm and 34.3 nm, respectively.

The resonant output spectrum for the photonic crystal resonator was recorded. The ratio of the output power at the resonant wavelength to the output power for a nonresonant wavelength was determined to be 0.44. Additionally, silicon crystal bus photonic waveguides that are fabricated using HSQ/XR-1541 (Dow-Corning Corporation) typically exhibit propagation losses around 2 dB/cm. Taking these into account, one may estimate the corresponding input power in the silicon bus photonic waveguide to be 630.4 µW. Thus, the power normalized stiffness for the resonant optical trapping apparatus in accordance with the foregoing first embodiment is determined to be 5.90 pN nm$^{-1}$ W$^{-1}$ and 5.55 pN nm$^{-1}$ W$^{-1}$ along the X and Y axes respectively thus giving a final radial trap stiffness of 2.86 pN nm$^{-1}$ W$^{-1}$.

By performing a detailed three dimensional finite element numerical analysis one may obtain theoretical trap stiffness values of 15.85 pN nm$^{-1}$ W$^{-1}$ (X-axis) and 8.14 pN nm$^{-1}$ W$^{-1}$ (Y-axis) resulting in a net radial trap stiffness of 5.38 pN nm$^{-1}$ W$^{-1}$. The results of these calculations are shown in FIG. 7a and FIG. 7b.

Figure 7:
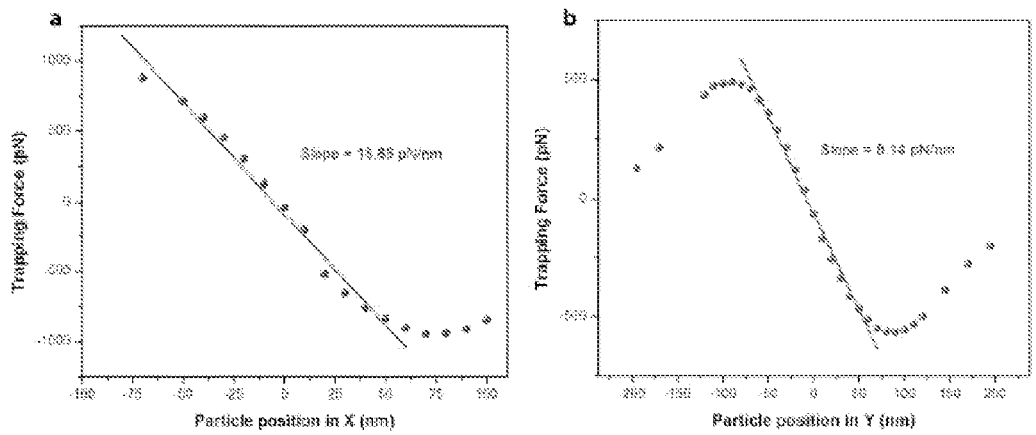
FIG. 7 shows a pair of graphs of Trapping Force versus Position in X or Y direction, related to Brownian motion suppression and trapping stiffness determination for nanoparticles in accordance with the first embodiment.

Within FIG. 7a and FIG. 7b, all forces are normalized to 1-W of input power in the waveguide. Within FIG. 7a, a force is experienced by a 200-nm trapped polystyrene nanoparticle as it is displaced along the length of the silicon photonic crystal resonator (X-axis). The zero X-axis value corresponds to the stable trapping position at the lobe centre. The slope in the linear region of the plot indicates a trapping stiffness of 15.85 pN nm$^{-1}$ W$^{-1}$ along the X-axis. Within FIG. 7b, the restoring force on the 200-nm particle is displaced in the Y-axis, normal to the length of the silicon photonic crystal resonator. The zero Y-axis value corresponds to the stable trapping position at the lobe centre. The slope of the linear region in the plot indicates a trapping stiffness of 8.14 pN nm$^{-1}$ W$^{-1}$ along the Y-axis.

II. Integrally Coupled Photonic Waveguide Based Photonic Crystal Resonator Optical Trapping Apparatus Fabricated from Silicon Nitride Materials Although conventional optical tweezers have been used for more than a decade, they are generally limited to trap dielectric particles lager than about 100 nm in diameter since the size of the focusing spot is limited by diffraction. Among different kinds of near-field optical trapping devices, photonic crystal resonators are especially promising for the trapping of even smaller nanoparticles and biomolecules since they can tightly confine electric fields in a very small volume. However, to utilize photonic crystal resonators to trap small biomolecules, in addition to optimizing the design of resonators to increase the field gradient, it is critical to minimize the heat generated in the vicinity of the devices so that the trapped biomolecules can function normally and that buoyancy driven flow and thermophoresis resulting from thermal heating does not affect the transport of biomolecules to the hot spots.

To reduce thermal heating, although almost all near-field optical trapping devices demonstrated so far, which are mostly made of silicon, are designed to operate at a wavelength of ~1550 nm, a second embodiment of a photonic crystal resonator optical trapping apparatus in accordance with the embodiments uses 1064 nm (or alternatively a wavelength in a range from about 700 to about 1200 nanometers) as the operating wavelength of a photonic crystal resonator since light of this wavelength is significantly less absorbed by water as compared to light of 1550 nm. Another benefit of using 1064 nm light in particular to trap biomolecules is that biomolecules are relatively more transparent in the spectrum around 750-1200 nm, which means photodamage to biomolecules is minimized when light within the spectrum mentioned above is used for trapping. Partly because of the choice of the operating wavelength, silicon nitride instead of silicon is used to fabricate the photonic crystal resonator optical trapping apparatus in accordance with the second embodiment. Silicon nitride is transparent in the visible and near-infrared spectrum and has optical and material properties suitable for near-field optical trapping applications.

Figure 8:
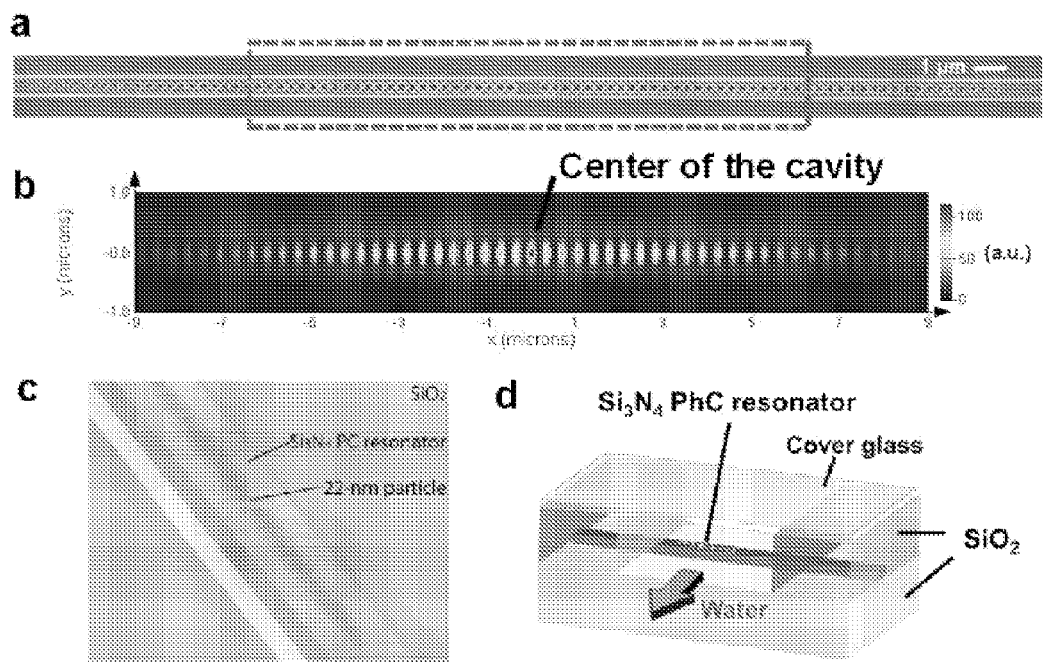
FIG. 8 shows a series of schematic plan-view and perspective-view diagrams of a photonic crystal resonator optical trapping apparatus in accordance with a second embodiment.

FIG. 8a and FIG. 8b show schematic plan-view diagrams of a silicon nitride photonic crystal resonator optical trapping apparatus in accordance with a second embodiment. In contrast with FIG. 1a and FIG. 2, a silicon nitride one-dimensional photonic crystal resonator is integral with a waveguide and may include up to at least about 53 holes (and also as few as about 10 holes) on either side of a cavity and a small hole at the center of the cavity. By adding the small hole to the cavity, an optical field intensity and thus a trapping stiffness within the silicon nitride photonic crystal resonator at the location of the hole are significantly increased. The sizes of the other holes may be modulated based on otherwise conventional design principles. The silicon nitride photonic crystal resonator and the integral photonic waveguides are made of silicon nitride (refractive index n=2.0), and a cladding layer at the bottom of the photonic crystal resonators and waveguides is made of silicon dioxide (refractive index n=1.45). The holes and the upper part of the photonic crystal resonators are exposed to an aqueous solution used in typical optical trapping experiments. FIG. 8c shows an image of the silicon nitride photonic crystal resonator optical trapping apparatus in accordance with the second embodiment having trapped thereupon a 22 nanometer polystyrene polymer nanoparticle. Finally, FIG. 8d shows the silicon nitride photonic crystal resonator optical trapping apparatus integrated into a fluid flow cell. According to three-dimensional finite-difference time-domain (FDTD) simulations, a resonant wavelength of the silicon nitride photonic crystal resonator in accordance with the second embodiment is ~1064 nm. The Q-factor is ~5000, and the mode volume is ~4.4 $(\lambda/n)^3$. Although the Q-factor of such a silicon nitride photonic crystal resonator is not high compared to other high-Q photonic crystal resonators demonstrated so far, experimental results show that such a silicon nitride photonic crystal resonator optical trapping apparatus in accordance with the second embodiment can effectively trap not only partially extended Lambda DNA molecules, but also 22-nm polystyrene polymer particles, quantum dots and Wilson disease proteins, which are all very difficult to optically trap using conventional optical tweezers. It is believed that the superior optical trapping capability of a silicon nitride photonic crystal resonator optical trapping apparatus in accordance with the second embodiment is strongly related to the observation that there is almost no thermal heating in the silicon nitride photonic crystal resonator under anticipated experimental conditions.

Figure 9:
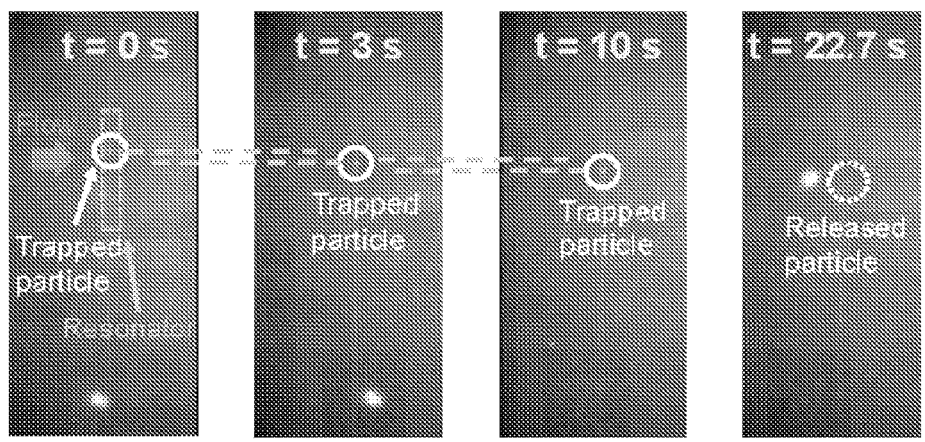
FIG. 9 shows a series of images illustrating fluorescent polymer nanoparticle trapping onto a silicon nitride photonic crystal resonator in accordance with the second embodiment.

FIG. 9 shows a series of fluorescence microscopy images that illustrates trapping and release of a 22-nm fluorescent polymer particle upon a silicon nitride photonic crystal resonator in accordance with the second embodiment. In each experiment a syringe pump was used to generate a flow in a flow chamber made by placing parafilm spacers between a coverslip and a fabricated chip. The surface of the fabricated chip was covered with casein to minimize non-specific binding. As shown in FIG. 9, the 22-nm polymer particle was trapped on the silicon nitride photonic crystal resonator when the 1064-nm laser light, which was TE-polarized, was coupled into the silicon nitride photonic waveguide integrally coupled with and connected to the silicon nitride photonic crystal resonator. The laser power coupled in to the silicon nitride photonic crystal resonator was less than 10 mW. The temperature of the laser diode was adjusted to fine-tune the wavelength of the laser so that the excitation wavelength matched the resonant wavelength of the silicon nitride photonic crystal resonator.

Figure 10:
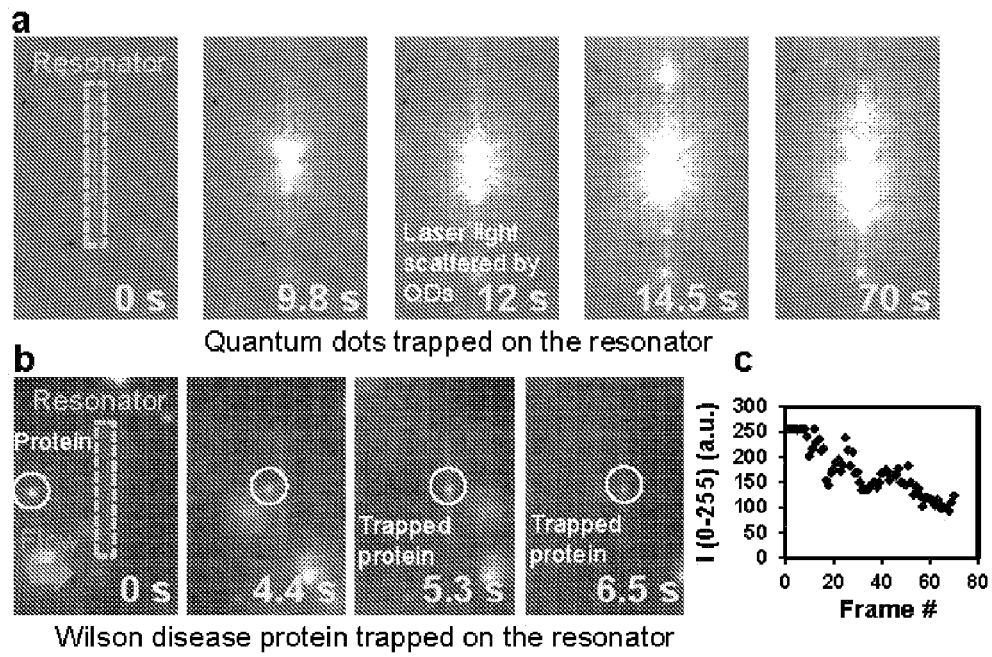
FIG. 10 shows a series of images illustrating quantum dot and Wilson disease protein trapping onto a silicon nitride photonic crystal resonator in accordance with the second embodiment.

Within this particular second embodiment, the trapped 22-nm polymer particle jumped from one place to another when they were moving on the silicon nitride photonic crystal resonator surface in the direction of the laser since the electric fields were much stronger between two adjacent holes than in the holes, except at the center of the cavity. After the laser was turned off, the trapped particle was released from the silicon nitride photonic crystal resonator, which suggests that the trapping of the polymer particle was caused by optical forces rather than non-specific binding. Similar optical trapping experiments were undertaken with streptavidin-coated CdSe/ZnS quantum dots (QDs), the cores of which were ~10-15 nm in diameter. Because of intrinsic fluorescence of silicon nitride, it was difficult to determine if QDs were trapped on the silicon nitride photonic crystal resonator by observing their fluorescence. Therefore, to observe trapping of QDs, an optical filter blocking 1064-nm laser light in front of a CCD camera was removed so that laser light scattered by optically trapped QDs could be seen by the CCD camera. As shown in FIG. 10a, QDs were trapped in and close to the cavity, which resulted in considerable scattering of 1064-nm light when the silicon nitride photonic crystal resonator was on resonance. However, when the laser filter was returned to block the 1064-nm light in front of the camera so that only fluorescent light could pass through, observed was only the QDs flowing in the flow chamber but not those trapped on the silicon nitride photonic crystal resonator. One possible explanation is that some kind of fluorescence quenching effect might cause the fluorescence of trapped QDs to disappear on the photonic crystal resonator surface.

Wilson disease proteins, which are only ~10 nm in diameter, were also trapped using a silicon nitride photonic crystal resonator in accordance with this second embodiment. These proteins have two sites that can be conjugated to Cy3 and Cy5 dyes. Since the filter cube used in the fluorescence microscope was for observing Cy5 but not Cy3, each protein seen by the CCD camera had either one or two Cy5 dyes. As shown in FIG. 10b, Wilson disease proteins were trapped when they were in close proximity to the silicon nitride photonic crystal resonator surface, and the Cy5 dyes were gradually photobleached in less than ~10 seconds. The one-stage decay of the fluorescence intensity, shown in FIG. 10c, suggests that the trapped protein is a single protein rather than aggregation of proteins. Finite element analysis shows that, under the experimental conditions used, a temperature increase at the resonator cavity of the silicon nitride photonic crystal resonator in accordance with the second embodiment is less than 0.1 K, which is small enough not to affect biological activities. In contrast, according to the numerical and experimental results, the temperature increase on a silicon photonic crystal resonator in accordance with the foregoing first embodiment that is excited by 1550-nm light and has a Q-factor of ~3000 is on the order of 60 K under similar experimental conditions. The significant difference in the temperature increase between the two photonic crystal resonator optical trapping apparatuses highlights the benefits of using silicon nitride photonic crystal resonators operating at 1064 nm over silicon photonic crystal resonators operating at 1550 nm for trapping small biomolecules.

Figure 11:
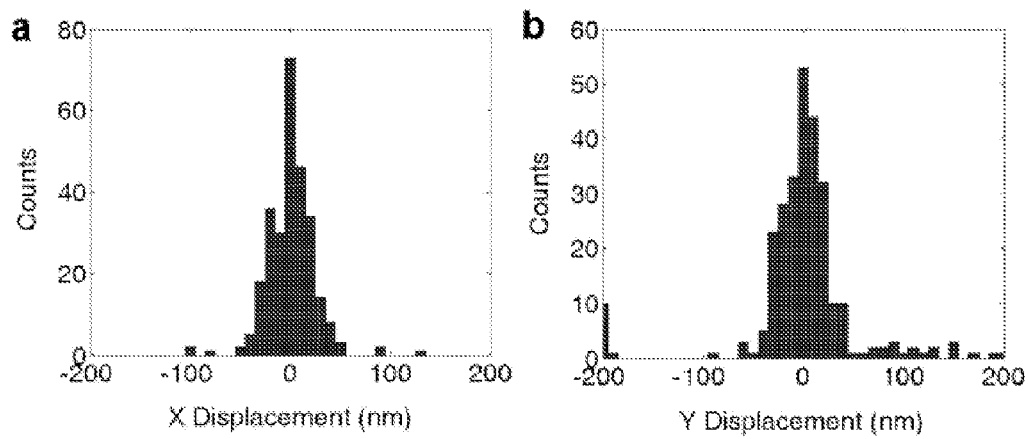
FIG. 11 shows graphs of Counts versus X-Displacement (FIG. 11a) and Y-Displacement (FIG. 11b) relating to Brownian motion of a 22 nanometer polystyrene polymer nanoparticle trapped on a silicon nitride photonic crystal resonator in accordance with the second embodiment.

To determine the trapping stiffness of the silicon nitride photonic crystal resonator in accordance with the second embodiment, the suppressed Brownian motion of a trapped 22-nm fluorescent polystyrene polymer particle was measured. FIG. 11a and FIG. 11b illustrate the histograms of the displacement of the trapped particle in the X and Y direction, respectively, when the laser power coupled into the resonator was ~6 mW. After correcting for the effect of the integration time of the CCD camera on the measurements of the particle motion, one may determine the standard deviation of the Brownian motion in the X and Y direction to be 75.7 nm and 94.4 nm, respectively. A stiffness of the optical trap in the X and Y direction was determined to be 0.12 $pN^{-1} W^{-1}$ and 0.08 $pN\,nm^{-1}\,W^{-1}$, respectively. Although it is difficult to compare the optical trapping capability of different optical trapping devices as, again, the trapping stiffness depends on the particle size, the observation that a photonic crystal resonator in accordance with the second embodiment can trap 15-nm QDs, 22-nm polymer particles, and 10-nm Wilson disease proteins already demonstrates the excellent trapping capability of the silicon nitride photonic crystal resonator in accordance with the second embodiment.

As demonstrated in this work, silicon nitride photonic crystal resonators operating at near infrared or visible wavelength can provide high optical trapping stiffness without generating much heat. The significantly reduced heat generation ensures that the trapped biomolecules can function normally and that the transport of biomolecules in a flow chamber would not be affected by thermal effects. Silicon nitride photonic crystal resonators in accordance with the second embodiment, such as the one used in this work, can be used to trap small biomolecules that are too small to be easily trapped using other optical trapping techniques for single-molecule studies.

Experimental

A. Device Fabrication

Silicon nitride photonic crystal resonator optical tapping devices and apparatuses in accordance with the second embodiment were fabricated using silicon wafers that included a 3.5 μm thick thermal oxide layer. A 250 nm-thick stoichiometric silicon nitride layer was deposited on the top of the thermal oxide layer using a low-pressure chemical vapour deposition (LPCVD) process. For example, ma-N 2403 electron beam photoresist was then spun on a wafer and then was patterned using a JEOL 9300 electron beam lithography system. The silicon nitride layer was then etched with the ma-N 2403 mask using an inductively coupled plasma reactive ion etch (ICP RIE) system, Oxford 100. Then, the lift-off process was used to create a patterned silicon dioxide layer, which was 3 μm-thick and was deposited using a magnetron sputtering deposition system, CVC 601, to cover the entire wafer except the area where the silicon nitride photonic crystal resonators were located.

B. Nanoparticle Sample Preparation 22-nm fluorescent polystyrene nanoparticles (Thermo Scientific) were suspended in 1× phosphate buffered saline solution (PBS), and streptavidin-coated QDs (Life Technologies) were suspended in 50 mM borate buffer solution (pH 7.4). Wilson disease proteins were suspended in HEPES buffer solution (60 mM HEPES, 110 mM NaCl, 1 mM EDTA, pH 7.4). Each of the three buffer solutions mentioned above also contained 0.05% (v/v) Tween 20 surfactant to reduce nonspecific binding. In addition, an oxygen scavenging system that consists of 50 nM protocatechuate-3,4-dioxygenase (PCD) and 2.5 mM protocatechuic acid (PCA) was introduced into the buffer solution right before each optical trapping experiment to increase the stability of fluorescent dyes.

C. Fluid Chamber Preparation

To prepare the flow chamber, two access holes were fabricated on a coverslip using a $CO_2$ laser system, and then Tygon tubing was affixed to the access holes with epoxy glue. Then, the coverslip, the fabricated chip, and a Parafilm spacer (which had a cut-out for the flow channel between the holes) were sandwiched together and briefly baked to create a sealed fluid chamber. A syringe driven by a syringe pump was used to inject the buffer solutions into the fluid chamber via Tygon tubing. Before introducing particles into the fluid chamber, the fluid chamber was first incubated with PBS solution that had 1 mg/ml casein for ~20 minutes to prevent nonspecific binding.

D. Optical Trapping Experiments

A 1064-nm fibre-coupled high power diode laser was used to provide the light source for optical trapping. Laser light was coupled into the silicon nitride photonic waveguide through a lensed fibre. The temperature of the laser diode was adjusted to fine-tune the centre wavelength of the laser diode, which shifted 0.3 nm per degree centigrade. Images were captured using a Hamamatsu ORCA-ER CCD camera.

E. Simulation and Data Analysis

The analysis of the Brownian motion of 22-nm polystyrene polymer nanoparticles was performed using the Video Spot Tracker software developed by CISMM at UNC Chapel Hill, and the three-dimensional FDTD simulation was carried out using FDTD Solutions (Lumerical Solutions, Inc.). The FIONA kernel of the Video Spot Tracker software was used to for particle tracking. The decay of the fluorescence intensity of the Wilson disease protein was determined using ImageJ software (US National Institutes of Health).

All references, including publications, patent applications, and patents cited herein are hereby incorporated by reference in their entireties to the extent allowable and to the same extent as if each reference was individually and specifically indicated to be incorporated by reference and was set forth in its entirety herein.

The use of the terms "a" and "an" and "the" and similar referents in the context of describing the invention (especially in the context of the following claims) is to be construed to cover both the singular and the plural, unless otherwise indicated herein or clearly contradicted by context. The terms "comprising," "having," "including," and "containing" are to be construed as open-ended terms (i.e., meaning "including, but not limited to,") unless otherwise noted. The term "connected" is to be construed as partly or wholly contained within, attached to, or joined together, even if there is something intervening.

The recitation of ranges of values herein are merely intended to serve as a shorthand method of referring individually to each separate value falling within the range, unless otherwise indicated herein, and each separate value is incorporated into the specification as if it was individually recited herein.

All methods described herein can be performed in any suitable order unless otherwise indicated herein or otherwise clearly contradicted by context. The use of any and all examples, or exemplary language (e.g., "such as") provided herein, is intended merely to better illuminate embodiments of the invention and does not impose a limitation on the scope of the invention unless otherwise claimed.

No language in the specification should be construed as indicating any non-claimed element as essential to the practice of the invention.

It will be apparent to those skilled in the art that various modifications and variations can be made to the embodiments without departing from the spirit and scope of the invention. There is no intention to limit the invention to the specific form or forms disclosed, but on the contrary, the intention is to cover all modifications, alternative constructions, and equivalents falling within the spirit and scope of the invention, as defined in the appended claims. Thus, it is intended that the present invention cover the modifications and variations of this invention provided they come within the scope of the appended claims and their equivalents.

Therefore, the embodiments are illustrative of the invention rather than limiting of the invention. Revisions and modifications may be made to methods, materials, structures and dimensions of a photonic crystal resonator optical trapping apparatus and a method for optical trapping using the photonic crystal resonator optical trapping apparatus while still providing a photonic crystal resonator optical trapping apparatus and a method for optical trapping using the photonic crystal resonator optical trapping apparatus in accordance with the embodiments, further in accordance with the accompanying claims.

What is claimed is:

1. An optical trapping apparatus comprising:
   a photonic waveguide located within a fluid channel over a substrate; and
   a photonic crystal resonator also located within the fluid channel and over the substrate, and coupled with the photonic waveguide, the photonic crystal resonator including a plurality of periodic structures located within the photonic crystal resonator, where the optical trapping apparatus is configured upon actuation to trap an analyte within a sample fluid within the fluid channel at a location selected from the group consisting of:
   the photonic waveguide; and
   sequentially at the photonic waveguide and the photonic crystal resonator.

2. The optical trapping apparatus of claim 1 wherein the photonic waveguide is separately coupled with the photonic crystal resonator.

3. The optical trapping apparatus of claim 2 wherein the photonic waveguide is separated from the photonic crystal resonator by a separation distance from about 50 to about 400 nanometers.

4. The optical trapping apparatus of claim 1 wherein the photonic waveguide is integrally coupled with the photonic crystal resonator.

5. The optical trapping apparatus of claim 1 wherein:
   each of the photonic waveguide and the photonic crystal resonator has a thickness from about 200 to about 500 nanometers; and
   each of the photonic waveguide and the photonic crystal resonator has a linewidth from about 200 to about 1000 nanometers.

6. The optical trapping apparatus of claim 1 wherein each of the photonic waveguide and the photonic crystal resonator comprises a single crystal silicon material.

7. The optical trapping apparatus of claim 1 wherein the optical trapping apparatus is configured to trap the analyte at the photonic waveguide.

8. The optical trapping apparatus of claim 1 wherein the optical trapping apparatus is configured to trap the analyte sequentially at the photonic waveguide and the photonic crystal resonator.

9. An optical trapping apparatus comprising:
a photonic waveguide located over a substrate; and
a photonic crystal resonator also located over the substrate and coupled with the photonic waveguide, the photonic crystal resonator including a plurality of periodic structures located within the photonic crystal resonator and comprising a photonic material having a resonant wavelength that is not absorbed by a sample fluid analyzed by the optical trapping apparatus, to thus inhibit heating of the sample fluid at the resonant wavelength of the photonic material when analyzing the sample fluid while using the optical apparatus.

10. The optical trapping apparatus of claim 9 wherein:
the sample fluid comprises water;
the photonic material comprises silicon nitride; and
the resonant wavelength is from about 700 to about 1200 nanometers.

11. The optical trapping apparatus of claim 10 wherein the resonant wavelength is about 1064 nanometers.

12. The optical trapping apparatus of claim 9 wherein the photonic waveguide is separately coupled with the photonic crystal resonator by a separation distance from about 50 to about 400 nanometers.

13. The optical trapping apparatus of claim 9 wherein the photonic waveguide is integrally coupled with the photonic crystal resonator.

14. The optical trapping apparatus of claim 9 wherein:
each of the photonic waveguide and the photonic crystal resonator has a thickness from about 200 to about 500 nanometers; and
each of the photonic waveguide and the photonic crystal resonator has a linewidth from about 200 to about 1000 nanometers.

15. An optical trapping method comprising:
introducing a sample fluid containing an analyte into a fluid channel of an optical trapping apparatus comprising:
the fluid channel located over a substrate;
a photonic waveguide located over the substrate and also within the fluid channel; and
a photonic crystal resonator also located over the substrate and also within the fluid channel, and also coupled with the photonic waveguide; and
actuating the optical trapping apparatus by introducing resonant photonic radiation into the photonic waveguide to trap the analyte from the sample fluid at a location selected from the group consisting of:
the photonic waveguide; and
sequentially at the photonic waveguide and the photonic crystal resonator.

16. The method of claim 15 wherein:
each of the photonic waveguide and the photonic resonator comprises a monocrystalline silicon material; and
the resonant photonic radiation has a wavelength about 1550 nanometers.

17. The method of claim 15 wherein the actuating traps the analyte at the photonic waveguide.

18. The method of claim 15 wherein the actuating traps the analyte sequentially at both the photonic waveguide and the photonic crystal resonator.

19. An optical trapping method comprising:
introducing a sample fluid containing an analyte into the fluid channel within an optical trapping apparatus comprising:
the fluid channel located over a substrate:
a silicon nitride photonic waveguide located over the substrate and also within the fluid channel; and
a silicon nitride photonic crystal resonator also located over the substrate, also within the fluid channel and also coupled with the photonic waveguide; and
actuating the optical trapping apparatus by introducing resonant photonic radiation into the photonic waveguide to trap the analyte from the sample fluid at a location selected from the group consisting of:
the photonic waveguide; and
sequentially at the photonic waveguide and the photonic crystal resonator.

20. The method of claim 19 wherein:
the photonic waveguide and the photonic crystal resonator comprise a silicon nitride material;
the analyte containing sample fluid comprises water;
the actuating uses resonant photonic radiation at a wavelength from about 700 to about 1200 nanometers; and
the analyte is trapped absent appreciable heating of the analyte containing sample fluid.

21. The method of claim 19 wherein the actuating uses the resonant photonic radiation at a wavelength of about 1064 nanometers.

22. The method of claim 19 wherein the actuating traps the analyte at the photonic waveguide.

23. The method of claim 19 wherein the actuating traps the analyte sequentially at the photonic waveguide and the photonic crystal resonator.

* * * * *